United States Patent [19]
Trombetta et al.

[11] Patent Number: 5,827,254
[45] Date of Patent: *Oct. 27, 1998

[54] ABSORBENT ARTICLE

[75] Inventors: Liberatore Antonio Trombetta; Dennis Allen Darby, both of Hamilton; Charlene Ann Hinds, Scarborough; Dhanraj Shantilal Patel, Mississauga, all of Canada

[73] Assignee: The Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 664,044

[22] Filed: Jun. 13, 1996

[51] Int. Cl.$^6$ .............................. A61F 13/15; A61F 13/20
[52] U.S. Cl. ........................................ 604/378; 604/385.1
[58] Field of Search ................................ 604/385.1, 378, 604/374, 358

[56] References Cited

U.S. PATENT DOCUMENTS

| | | | |
|---|---|---|---|
| 1,946,626 | 2/1934 | Jurgensen | 128/290 |
| 2,939,461 | 6/1960 | Joa | 128/290 |
| 3,371,667 | 3/1968 | Morse | 604/378 |
| 3,400,718 | 9/1968 | Saijo | 128/291 |
| 3,572,342 | 3/1971 | Lindquist et al. | 128/287 |
| 4,029,101 | 6/1977 | Chesky et al. | 604/378 |
| 4,410,324 | 10/1983 | Sabee | 604/368 |
| 4,576,596 | 3/1986 | Jackson et al. | 604/370 |
| 4,636,209 | 1/1987 | Lassen | 604/378 |
| 4,670,011 | 6/1987 | Mesek | 604/385.1 |
| 4,753,645 | 6/1988 | Johnson | 604/378 |
| 4,781,711 | 11/1988 | Houghton et al. | 604/378 |
| 4,988,344 | 1/1991 | Reising et al. | 604/368 |
| 4,988,345 | 1/1991 | Reising | 604/368 |
| 4,994,052 | 2/1991 | Kimura | 604/355 |
| 5,304,161 | 4/1994 | Noel et al. | 604/385.1 |
| 5,352,217 | 10/1994 | Curro | 604/378 |
| 5,578,025 | 11/1996 | May | 604/385.1 |

FOREIGN PATENT DOCUMENTS

| | | |
|---|---|---|
| 0 222 585 | 5/1987 | European Pat. Off. . |
| 0 471 114 A2 | 2/1992 | European Pat. Off. . |
| 0 705 587 A2 | 4/1996 | European Pat. Off. . |
| 1 513 055 | 6/1978 | United Kingdom . |
| 2 233 235 | 1/1991 | United Kingdom . |
| WO 90/14063 | 11/1990 | WIPO . |
| WO 92/11830 | 7/1992 | WIPO . |
| WO 94/02092 | 2/1994 | WIPO . |
| WO 94/06385 | 3/1994 | WIPO . |
| WO 96/01095 | 1/1996 | WIPO . |
| WO 96/40029 | 12/1996 | WIPO . |

*Primary Examiner*—John G. Weiss
*Assistant Examiner*—Bruce E. Snow
*Attorney, Agent, or Firm*—Thomas J. Osborne, Jr.; David M. Weirich; Jacobus C. Rasser

[57] ABSTRACT

A disposable absorbent article such as an incontinence pad that is both comfortable and suitable for absorbing and containing large volumes of body liquids rapidly without leakage, especially a subsequent gush of liquid. The absorbent article has a pair of end regions, and a central region disposed between the end regions. The central region includes a pair of spaced apart longitudinal side portions and a central portion disposed between the longitudinal side portions. The absorbent article includes a liquid pervious topsheet, a liquid impervious backsheet joined to the topsheet, an absorbent core positioned between the topsheet and backsheet, and an acquisition component positioned between the topsheet and the absorbent core. The acquisition component has a total void volume. The portion of the acquisition component with the central region provides at least about 50% of the total void volume of the absorbent article. A portion of the absorbent core is folded upon the acquisition component along a first pair of generally parallel longitudinally extending fold lines to form a pair of resilient absorbent members which encapsulate the acquisition component within the longitudinal side portions. The resilient absorbent members are arranged in a longitudinally spaced relation to each other between the acquisition component and the topsheet. The absorbent article has a total absorptive capacity. The central region provides at least about 50% of the total absorptive capacity and the longitudinal side portions provide at least about 70% of the central regions absorptive capacity.

19 Claims, 4 Drawing Sheets

ABSORBENT ARTICLE

FIELD OF THE INVENTION

The present invention relates to absorbent articles such as incontinence pads, and more particularly, to absorbent articles which are comfortable yet capable of rapidly accepting and containing large volumes of liquids.

BACKGROUND OF THE INVENTION

There is a growing awareness of the lack of satisfactory products designed for mobile persons with incontinent infirmities. While sanitary napkins, pantiliners, disposable briefs and diapers are available for the mobile incontinent person, such products are not satisfactory from either a comfort or a protection standpoint. Catamenial products such as pantiliners and sanitary napkins are very comfortable to use. However, these products fail to achieve a satisfactory level of containment for high void levels of urine. While diapers and briefs meet the containment needs of the incontinent person, these products lack the comfort and discreteness available from sanitary napkins and pantiliners.

Thus, it is desirable to provide an absorbent article such as an incontinence pad that is comfortable and discrete, yet provides superior protection and containment. In order to achieve the goal of providing such an absorbent article, it is necessary that the absorbent article be capable of rapidly accepting and containing a large volume of liquid within a small surface area; rapidly distributing the liquid efficiently throughout the product; conforming to the body of the wearer; maintaining good body contact (i.e., the maintenance of the absorbent article in close proximity to and in conformity with the body of the wearer); and maintaining its integrity even when wetted so as to be effective to accept and contain a subsequent discharge or gush of liquid and to prevent rewet (i.e., recontact of liquids contained in the absorbent article with the skin of the wearer due to forces that squeeze the liquid out of the absorbent article).

One of the methods for enhancing the absorptivity of such products is to provide a void space or reservoir that is located near the top surface of the article. Examples of these type of products are disclosed in U.S. Pat. No. 3,364,931 issued Jan. 23, 1968 to W. F. Hirsch; U.S. Pat. No. 4,029,101 issued Jun. 14, 1977 to Chesky et al., and U.S. Pat. No. 4,501,586 issued Feb. 26, 1985 to Holtman. Such articles, while providing some measure of increased ability to accept large volumes of liquid, are often incapable of both effectively accepting a subsequent discharge or gush of liquid and preventing rewet. This is due to the lack of integrity or from retention capacity of the materials after being wetted. Absorbent cores such as those formed of creped wadding or cellulosic fibers have a tendency to split, ball or lump when wetted. They thereby become relatively shapeless and non-form-sustaining. These elements also tend to flatten out and become compacted when subjected to forces. Because an absorbent article is subject to various forces during use, the article will tend to lose its shape when wetted. Thus, it will not conform to the body of the wearer resulting in discomfort for the wearer. In addition, the wetted and compressed absorbent core will have lost its ability to absorb a subsequent discharge or gush of liquid resulting in an increased likelihood of leakage and failure of the product. Further, because the void space or reservoir tends to lose its size and shape, not only is there a decreased ability to contain high volumes, but there is also an increased danger of rewet as the overwrap is no longer spaced away from the absorbent core.

Thus, there is a need to provide an absorbent article wherein the article will retain its shape after being wetted so as both to remain comfortable and to be able to rapidly absorb and contain a subsequent gush of liquid without increasing the likelihood of leakage or rewet. Accordingly, it would be advantageous to provide an absorbent article that retains its shape after being wetted without a loss in comfort or absorbent capacity. It would also be advantageous to provide an article having increased absorption and increased comfort.

Given the geometry of absorbent articles, a width dimension which is smaller than the length dimension, leakage typically occurs along the longitudinal side edges of the absorbent article as bodily fluid deposited in the center of the absorbent article spreads radially reaching the longitudinal side edges prior to reaching the transverse end edges. Thus, there is a need to provide an absorbent article which reduces the likelihood of side leakage.

Another method for increasing the absorbency of absorbent articles is to provide them with absorbent gelling materials. Absorbent gelling materials are polymeric materials which are capable of absorbing large quantities of liquids and which are further capable of retaining such absorbed liquids under moderate pressures. These absorption characteristics of absorbent gelling materials make such materials especially useful for incorporation into absorbent articles such as incontinence pads.

The effectiveness of absorbent gelling materials in disposable absorbent articles can be quite dependent upon the form, position and/or manner in which the absorbent gelling material is incorporated into the absorbent article. In some cases, for example, the effectiveness of absorbent gelling material absorption in absorbent articles can be adversely affected by a phenomenon called "gel blocking". The term gel blocking describes a situation that occurs when an absorbent gelling material particle, film, fiber, composite, etc. is wetted. Upon wetting, the surface of the absorbent gelling material swells and inhibits liquid transmission to the interior of the absorbent material. Wetting of the interior subsequently takes place via a very slow diffusion process. In practical terms, this means that absorption of liquid by the article is much slower than discharge of liquid to be absorbed, and failure of the absorbent article may take place well before the absorbent gelling material in the absorbent article is fully saturated.

Thus, there is a continuing need to identify absorbent gelling material containing absorbent articles wherein the absorbent gelling material is especially effective and efficient in performing its intended function of holding discharged body liquids without interfering with the acquisition and distribution of body liquids by and within the article. Absorbent gelling materials are generally significantly more expensive than readily available absorbent fiber materials (e.g. cellulose fibers). Accordingly it would be advantageous to provide articles wherein either absorbent capacity of the absorbent gelling material-containing article can be improved or wherein a given absorbent capacity of an article can be maintained while efficiently utilizing the relatively expensive absorbent gelling material. It would also be advantageous to provide articles wherein the liquid-storing absorbent gelling material does not adversely affect the ability of the absorbent article to quickly acquire discharged body liquids.

Therefore, it is an object of the present invention to provide an absorbent article which is able to rapidly accept and contain a large void of body liquids without leakage.

It is another object of the present invention to provide an absorbent article having improved comfort in both the wet and dry state for the wearer.

It is another object of the present invention to provide an absorbent article which reduces the incidence of side leakage.

These and other objects of the invention will be more readily apparent when considered and referenced to the following description and when taken in conjunction with the accompanying drawings.

SUMMARY OF THE INVENTION

The present invention provides a disposable absorbent article such as an incontinence pad that is both comfortable and suitable for absorbing and containing large volumes of body liquids rapidly without leakage, especially a subsequent gush of liquid. The absorbent articles of the present invention have a pair of end regions, and a central region disposed between the end regions. The central region comprises a pair of spaced apart longitudinal side portions and a central portion disposed between the longitudinal side portions. The absorbent article comprises a liquid pervious topsheet, and a liquid impervious backsheet joined with the topsheet. An acquisition component is positioned between the topsheet and the backsheet. The acquisition component has a total void volume. The portion of the acquisition component with the central region provides at least about 50% of the total void volume of the absorbent article. An absorbent core is positioned between the acquisition component and the backsheet. A portion of the absorbent core is folded upon the acquisition component along a first pair of generally parallel longitudinally extending fold lines to form a pair of resilient absorbent members which encapsulate the acquisition component within the longitudinal side portions. The resilient absorbent members are arranged in a longitudinally spaced relation to each other between the acquisition component and the topsheet. The absorbent article has a total absorptive capacity. The central region provides at least about 50% of the total absorptive capacity. The longitudinal side portions provide at least about 70% of the central regions absorptive capacity.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

DETAILED DESCRIPTION OF THE INVENTION

Figure 1:
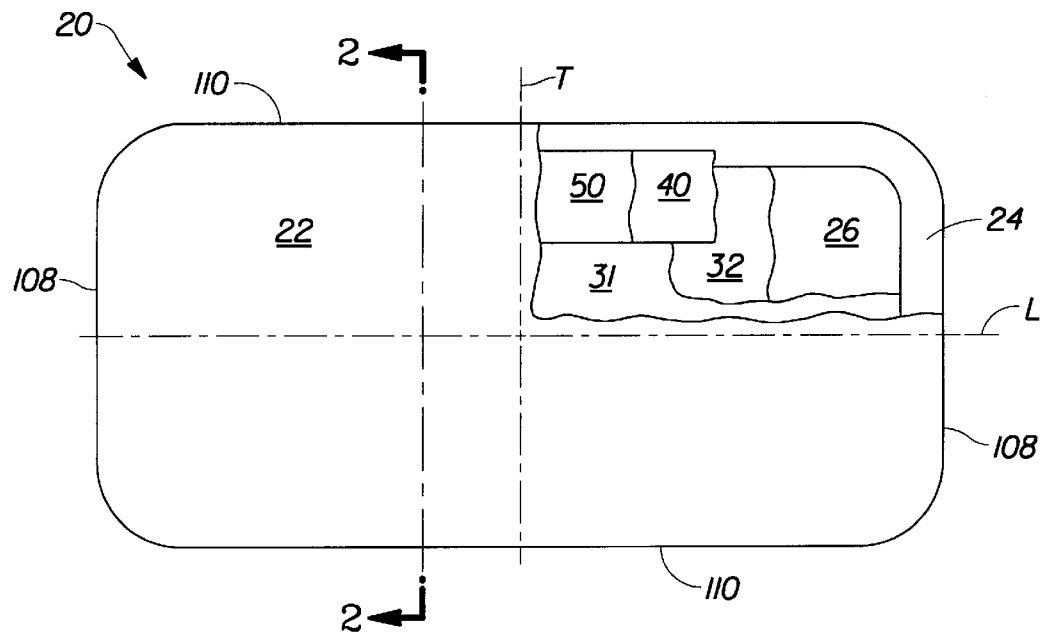
FIG. 1 is a plan view of an incontinence pad of the present invention having portions cut away to reveal the underlying structure.

As used herein, the term "disposable absorbent article" refers to articles which absorb and contain body liquids and more specifically refers to articles which are placed against or in proximity to the body of the wearer to absorb and contain the various liquids discharged from the body, and which are intended to be discarded after a single use (i.e., they are not intended to be laundered or otherwise restored and reused). A preferred embodiment of the disposable absorbent article of the present invention, incontinence pad 20, is shown in FIG. 1 and in cross-sectional view in FIG. 2. As used herein, the term "incontinence pad" refers to a garment generally worn by incontinent persons by adhesively attaching the pad directly to the crotch region of the wearer's undergarment. It should be understood, however, that the present invention is also applicable to other disposable absorbent articles such as incontinence briefs, diapers, sanitary napkins, and the like.

FIG. 1 is a plan view of the incontinence pad 20 of the present invention with portions of the structure being cut away to more clearly show the construction of the incontinence pad 20 and with the portion of the incontinence pad 20 which faces or contacts the wearer, oriented towards the viewer. As shown in FIG. 1, the incontinence pad 20 preferably comprises a liquid pervious topsheet 22, a liquid impervious backsheet 24 joined with the topsheet 22, an absorbent core 25 positioned between the topsheet 22 and the backsheet 24, an acquisition component 30 positioned between the topsheet 22 and the absorbent core 25, and a pair of resilient absorbent members 40 disposed one on each side of the incontinence pad 20 in a spaced relation to one another between the topsheet 22 and the acquisition component 30, and a rewet barrier 50 positioned between the resilient absorbent members 40 and the topsheet 22.

Figure 2:
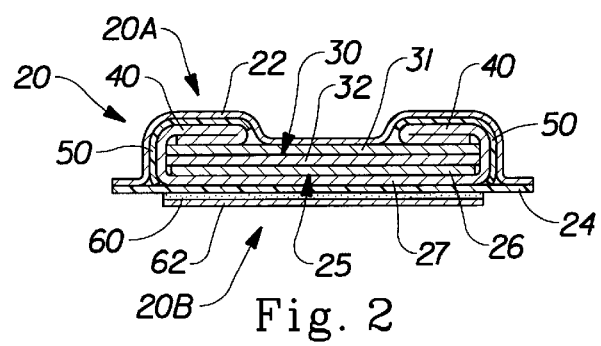
FIG. 2 is a cross-sectional view of the incontinence pad of the present invention taken along section line 2—2 of FIG. 1.

As shown in FIG. 2, the absorbent core 25 comprises two distinct layers 26 and 27, respectively. The acquisition component 30, as shown in FIG. 2, comprises two distinct layers 31 and 32, respectively. The rewet barriers 50 cover portions of each of the resilient absorbent members 40 to provide a barrier in order to contain liquids within the incontinence pad 20. Secured along the bottom of the incontinence pad 20 on the backsheet 24 is an adhesive attachment means 60 that is covered by a removable release liner 62.

It should be understood for the purposes of this invention that the term "layers" does not necessarily limit the invention to single layers or sheets of material. Thus, each of the layers may actually comprise laminates for combinations of several sheets or webs of the requisite type of the materials as hereinafter described. Thus, as used herein, the term "layer" includes the terms "layers" and "layered".

Figure 3:
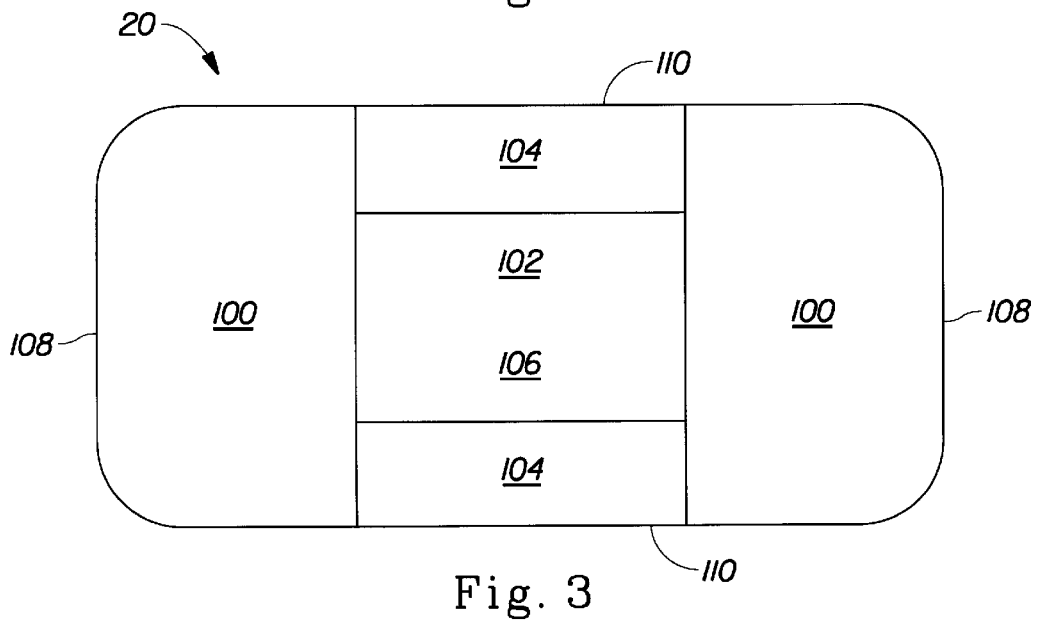
FIG. 3 is a simplified plan view depicting the various regions and portions of the incontinence pad of the present invention.

FIG. 3 shows a simplified plan view of the incontinence pad 20 of FIG. 1 depicting the various regions and portions of the incontinence pad 20 and their positioning with respect to each other. The incontinence pad 20 comprises a pair of end regions 100 and a central or insult accepting region 102. The central region 102 is disposed between the respective end regions 100. The end regions 100 extend longitudinally outwardly from the central region 102 to form portions of the end edges 108.

Figure 5:
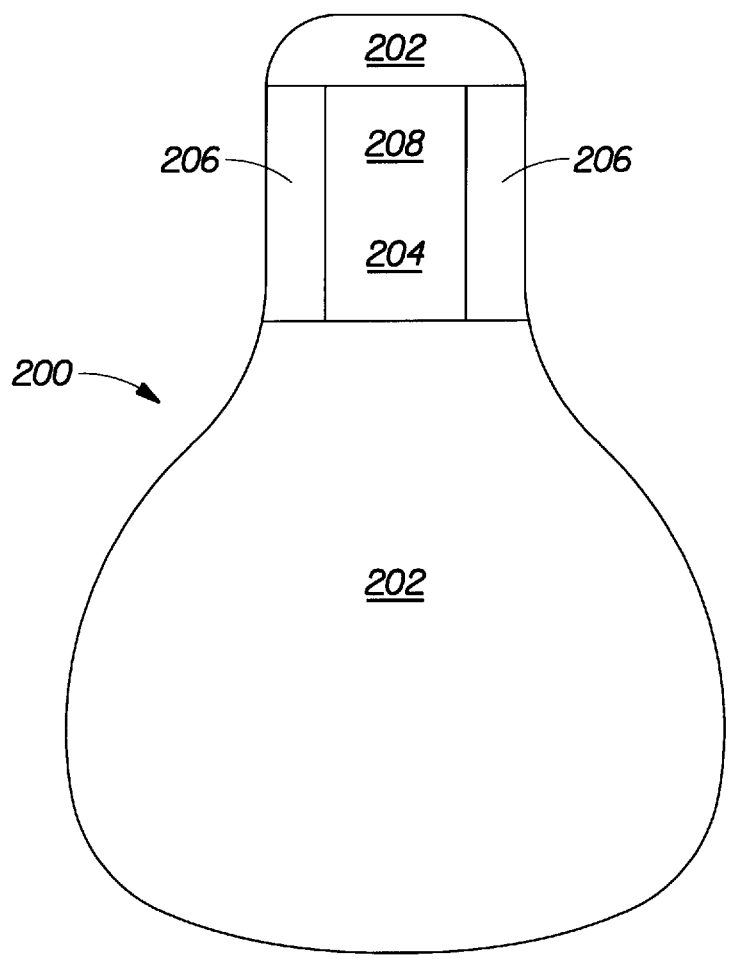
FIG. 5 is a plan view of another embodiment of an incontinence pad of the present invention.

While in FIG. 3 the central or insult accepting region 102 is shown to be positioned in the center of the incontinence pad 20, the exact location of the insult accepting region 102 is not critical to the performance of the incontinence pad 20. For example, in some embodiments the insult accepting region 102 may be positioned near one of the end edges of the incontinence pad 20. Referring now to FIG. 5, the incontinence pad 200 comprises a pair of end regions 202 and a central or insult accepting region 204. The central or insult accepting region 204 comprises a pair of longitudinal side portions 206 and a central portion 208. The central region 204 is disposed between the respective end regions 202. The end regions 202 extend longitudinally outwardly from the central region 204. Alternatively, the central region 204 may be positioned such that it forms a portion of one of the end edges of the incontinence pad.

Referring again to FIG. 3, the central region 102 preferably comprises from at least about one-fourth to about two-thirds of the total longitudinal length of the incontinence pad 20. Most preferably, the central region 102 comprises about one-third of the total longitudinal length of the incontinence pad 20.

The central region 102 comprises a pair of spaced apart longitudinal side portions 104 and a central portion 106 disposed between the longitudinal side portions 104. The longitudinal side portions 104 extend laterally outwardly from the central portion 106 to form portions of the longitudinal side edges 110.

Preferably, each longitudinal side portion 104 comprises from at least about one-eighth to about one-third of the total transverse width of the central region 102. Most preferably, each longitudinal side portion 104 comprises about one-fourth of the total transverse width of the central region 102.

The transverse width of the central portion 106 is critical to the rapid acquisition characteristics of the incontinence pad 20. If the width of the central portion 106 is too small, the incontinence pad 20 will be unable to rapidly collect and contain large gushes of liquid. Preferably, the central portion 106 comprises from at least about one-third to about three-fourths of the total transverse width of the central region 102. Most preferably, the central portion 106 comprises about one-half of the total transverse width of the central region 102.

Referring again to FIGS. 1 and 2, the incontinence pad 20 has two surfaces, a body-contacting surface or body facing surface 20A and a garment facing surface 20B. The incontinence pad 20 is shown in FIG. 1 as viewed from its body facing surface 20A. The body facing surface 20A is intended to be worn adjacent to the body of the wearer while the garment facing surface 20B is on the opposite side and is intended to be placed adjacent to the wearer's undergarments when the incontinence pad 20 is worn.

The incontinence pad 20 has two centerlines, a longitudinal centerline L and a transverse centerline T. The term "longitudinal", as used herein, refers to a line, axis or direction in the plane of the incontinence pad 20 that is generally aligned with (e.g., approximately parallel to) a vertical plane which bisects a standing wearer into left and right body halves when the incontinence pad 20 is worn. The terms "transverse" or "lateral" as used herein, are interchangeable and refer to a line, axis or direction which lies within the plane of the incontinence pad 20 that is generally perpendicular to the longitudinal direction.

The topsheet 22 is compliant, soft feeling and non-irritating to the wearer's skin. Further, the topsheet 22 is liquid pervious permitting liquids (e.g., menses and/or urine) to readily penetrate through its thickness. A suitable topsheet may be manufactured from a wide range of materials, such as woven and nonwoven materials; polymeric materials such as apertured formed thermoplastic films, apertured plastic films, and hydroformed thermoplastic film; porous foams; reticulated foams; reticulated thermoplastic film; and thermoplastic scrims. Suitable woven and nonwoven materials can be comprised of natural fibers (e.g., wood or cotton fibers), synthetic fibers (e.g., polymeric fibers such as polyester, polypropylene, polyethylene fibers or bicomponent fibers) or from a combination of natural and synthetic fibers. A preferred topsheet comprises an apertured formed film. Apertured formed films are preferred for topsheets because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135 issued to Thompson on Dec. 30, 1975; U.S. Pat. No. 4,324,246 issued to Mullane et al. on Apr. 13, 1982; U.S. Pat. No. 4,342,314 issued to Radel et al. on Aug. 3, 1982; U.S. Pat. No. 4,463,045 issued to Ahr on Jul. 31, 1984; and U.S. Pat. No. 5,006,394 issued to Baird on Apr. 9, 1991. Each of these patents are incorporated herein by reference. A preferred topsheet for the present invention is the formed film described in one or more of the above patents and marketed on sanitary napkins by The Procter & Gamble Company of Cincinnati, Ohio as "DRI-WEAVE".

In a preferred embodiment of the present invention, the body facing surface of the formed film topsheet is hydrophilic so as to help liquid to transfer through the topsheet faster than if the body facing surface was not hydrophilic so as to diminish the likelihood that bodily fluid will flow off of the topsheet rather than flowing into and being absorbed by the absorbent core. In a preferred embodiment, surfactant is incorporated into the polymeric materials of the formed film topsheet such as is described in U.S. patent application Ser. No. 07/794,745, "Absorbent Article Having A Nonwoven And Apertured Film Coversheet" filed on Nov. 19, 1991 by Aziz et al., which is incorporated herein by reference. Alternatively, the body facing surface of the topsheet can be made hydrophilic by treating it with a surfactant such as described in U.S. Pat. No. 4,950,264 issued to Osborn on Aug. 21, 1990, incorporated herein by reference.

Another suitable topsheet is a composite or "hybrid" topsheet structure. The hybrid topsheet generally comprises a longitudinally oriented central zone and longitudinal side regions located laterally outboard of the central zone. The hybrid topsheet structure preferably comprises an apertured thermoplastic film in the central zone of the hybrid topsheet structure and a less plastic-like outer covering that forms the longitudinal side portions. Such a topsheet is useful for improving the skin feel and comfort of the topsheet made of apertured plastic film. In particular, such a topsheet reduces the tendency for apertured plastic films to feel hot, sweaty and sticky. This is especially useful in the case of larger absorbent articles wherein there is a large portion of the topsheet which is in contact with the wearer's body. Hybrid topsheet structures are described generally in PCT Publication No. 93/09744 assigned to The Procter & Gamble Company which published May 27, 1993, in the name of Sugahara et al., which is incorporated herein by reference.

Another suitable topsheet comprises an upper layer constituted by a nonwoven textile of synthetic fibers, an intermediate layer constituted by a film material and a lower layer constituted by a nonwoven layer of textile of synthetic fibers. An example of such a topsheet is described in U.S. Pat. No. 4,780,352 issued to Palumbo on Oct. 25, 1988, which is incorporated herein by reference.

The backsheet 24 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contrast of the human body. The backsheet 24 prevents the exudates absorbed and contained in the absorbent core from wetting articles which contact the incontinence pad 20 such as pants, pajamas, and underpants. The backsheet 24 may thus comprise a woven or nonwoven material, polymeric films such as thermoplastic films of polyethylene or polypropylene, or composite materials such as a film-coated nonwoven material. Preferably, the backsheet 24 is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Tredegar Corporation, of Terre Haute, Ind., under the designation XP-39385. The backsheet is preferably embossed and/or matte finish to provide a more cloth-like appearance. Further, the backsheet 24 may permit vapors to escape from the absorbent core (i.e., breathable), while still preventing exudates from passing through the backsheet 24.

The backsheet 24 and the topsheet 22 are preferably joined to each other and other components or layers of the incontinence pad 20 by attachment means (not shown) such as those well known in the art. For example, the backsheet 24 and/or the topsheet 22 may be secured to each other or to other components by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesives as is disclosed in U.S. Pat. No. 4,573,986 issued to Minetola et al. on Mar. 4, 1986, and which is incorporated herein by reference. An exemplary attachment means of an open patterned network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zieker et al. on Nov. 22, 1978; and U.S. Pat. No. 4,842,666 issued to Werenicz on Jun. 7, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The acquisition component 30 serves several functions including accepting a high rate of fluid intake, serving as a temporary reservoir for the fluid, efficiently transporting fluids over and into the absorbent core, and draining substantially completely into the absorbent core in order to remain empty for subsequent fluid loadings. There are several reasons why efficiently transporting bodily fluids is important, including providing a more even distribution of bodily fluids throughout the absorbent core. The transportation referred to herein may encompass the transportation of liquids in one, two, or all directions (i.e., in the X-Y plane and/or in the Z-direction). In addition, the acquisition component 30 must resist collapse when wet so that it maintains its performance through multiple loadings. The acquisition component also preferably provides a resilient form retaining member within the interior of the incontinence pad 20. The acquisition component also allows liquid contact with large surface areas with the underlying absorbent core. This element preferably does all these things while also remaining thin.

The acquisition component 30 serves to drain liquids through the topsheet and provide void volume so that the underlying absorbent core (which has high storage capacity, but relatively slow rate of absorbency) will have time to absorb bodily fluids deposited thereon. Furthermore, since the point of insult typically occurs within the central region 102 of the incontinence pad 20, it is important that the portion of the acquisition component 30 located within the central region 102 provide sufficient void volume to handle and distribute repeated gushes of liquid. Since the point of insult typically does not occur within the end regions 100, the requirements for void volume in the end regions 100 is not as stringent as that required of the central region 102. Thus, the acquisition component within the central region 102 preferably provides from at least about 50% to about 100% of the total void volume of the acquisition component 30, more preferably from at least about 60% to about 80%, with 70% being the most preferred.

As shown in FIGS. 1 and 2, the acquisition component 30 comprises two distinct layers 31 and 32. Each layer 31 and 32 can be of any desired shape. Suitable shapes include for example, circular, rectangular, triangular, trapezoidal, oblong, dog-boned, hourglass, oval, asymmetric, etc. In the embodiment shown in FIGS. 1 and 2, the acquisition layer 31 has an hourglass shape and the acquisition layer 32 has a rectangular shape.

The uppermost acquisition layer 31 preferably has a longitudinal length at least equal to that of the central region 102. The uppermost acquisition layer 31 may have a longitudinal length greater than that of the central region 102 such that the uppermost acquisition layer 31 extends into the end regions 100 of the incontinence pad 20. The acquisition layer 31 preferably has a transverse width at least equal to that of the central portion 106. The uppermost acquisition layer 31 may have a transverse width greater than that of the central portion 106 such that the uppermost acquisition layer 31 extends into the longitudinal side regions 104 of the incontinence pad 20.

The lowermost acquisition layer 32 preferably has a longitudinal length at least equal to that of the central region 102. The lowermost acquisition layer 32 may have a longitudinal length greater than that of the central region 102 such that the lowermost acquisition layer 32 extends into the end regions 100 of the incontinence pad 20. The lowermost acquisition layer 32 preferably has a transverse width at least equal to that of the central portion 106. The lowermost acquisition layer 32 may have a transverse width greater than that of the central portion 106 such that the lowermost acquisition layer 32 extends into the longitudinal side regions 104 of the incontinence pad 20.

The uppermost acquisition layer 31 is shown in FIG. 1 to have a longitudinal length greater than that of the lowermost acquisition layer 32. Alternatively, the uppermost acquisition layer 31 may have a longitudinal length less than or equal to that of the lowermost acquisition layer 32.

In the embodiment shown in FIG. 2, the acquisition component 30 comprises two acquisition layers 31 and 32, respectively. Alternatively, the acquisition component 30 may comprise a single layer or multiple layers, for example, three, four, five or more layers.

The acquisition components may be comprised of several different materials including nonwoven or woven webs of synthetic fibers including polyester, polypropylene, or polyethylene; natural fibers including cotton or cellulose; blends of such fibers; or any equivalent materials or combinations of materials. Suitable nonwoven webs include bonded carded webs, spunbonded webs, meltblown webs, spunlaced webs, stitch-bonded webs, and thermally bonded air laid webs. The acquisition component may be joined with the topsheet, each other, and the absorbent core by any conventional means for joining webs together such as adhesives, heat bonds, pressure bonds, ultrasonic bonds, dynamic mechanical bonds, or any other suitable attachment means or combinations of these attachment means as are known in the art.

If the acquisition component is a nonwoven web, the nonwoven web may be a spunbonded web, a meltblown web, a bonded carded web, a spunlaced web, a stitch-bonded web, or a thermally bonded air laid web. The nonwoven web may be made of fiber forming polymers such as, for example, polyesters, polyamines, and polyolefins. Exemplary polyolefins include one or more of polypropylene, polyethylene, ethylene copolymers, propylene copolymers, and butene copolymers. In another embodiment, the acquisition component may be multi-layer material having, for example, at least one layer of a spun bonded web joined to at least one layer of a meltblown web, a bonded carded web, a thermally bonded air laid web, or other suitable material. Alternatively, the nonwoven layer may be a single layer of material such as, for example, a spunbonded web or a meltblown web. The nonwoven web may also be a composite made up of a mixture of two or more different fibers or a mixture of fibers and particles. Such mixtures may be formed by adding fibers and/or particulates to the gas stream in which the meltblown fibers or spunbonded fibers are carried so that an intimate entangled commingling of fibers and other materials, e.g., wood pulp, staple fibers, superabsorbent materials, and particles corresponding to the collection of the fibers. In another preferred embodiment, the nonwoven web may be comprised of bicomponent fibers. The bicomponent fibers preferably are a thermal bondable bicomponent fiber having an inner core component and an outer sheath component where the inner core component has a higher melting point than the outer sheath component. The ability of the sheath to melt during thermal bonding gives the fiber a heat feasible characteristic. The fiber itself is typically hydrophobic, but can be made hydrophilic by incorporating a surfactant into the sheath of the bicomponent fiber and/or by treating the external surface of the sheath with a surfactant. Exemplary bicomponent fibers and processes for producing the same are described in European Patent Application No. 0 340 763, published Nov. 8, 1989 in the name of Hansen et al. Exemplary acquisition layers having bicomponent fibers are described in U.S. Pat. No. 5,231,122 issued to Palumbo et al. on Jul. 27, 1983; and in International Publication No. WO 94/28838, published Dec. 22, 1994 in the name of Palumbo, et al., each of which is incorporated herein by reference.

The fibrous acquisition component may comprise a composite of bicomponent fibers and other fibers such as rayon, monocomponent synthetic fibers, and tricomponent synthetic fibers. For example the acquisition component may comprise a blend of 75% bicomponent fibers and 25% rayon fibers. Other suitable blends of bicomponent fibers and rayon fibers may also be used. The fibrous acquisition component should also have an operable level of density and basis weight to rapidly acquire and then drain liquid surges into the underlying absorbent core, thus remaining relatively empty to receive subsequent liquid surges. The fibrous acquisition component should have sufficient void volume capacity to temporarily retain the amount of liquids that is typically discharged by a wearer during a surge of liquid into the incontinence pad. Insufficient void volume capacity may result in excessive pooling of liquid against the wearer's skin or excessive run-off of liquid.

The basis weight of the acquisition component is preferably within the range of from about 10 g/m$^2$ to about 300 g/m$^2$, more preferably from about 20 g/m$^2$ to about 200 g/m$^2$, and most preferably from about 30 g/m$^2$ to about 80 g/m$^2$. The fibrous acquisition component has a thickness of from about 1 mm to about 10 mm, more preferably from about 1.5 mm to about 6 mm, still more preferably from about 1.7 mm to about 4.5 mm, and more preferably from about 2 mm to about 4 mm, as measured under a pressure of 2 kPa.

The fibrous acquisition component has a bulkiness of from about 10 cm$^3$/g to about 100 cm$^3$/g, more preferably a bulk mass of from about 15 cm$^3$/g to about 65 cm$^3$/g, still more preferably from about 20 cm$^3$/g to about 60 cm$^3$/g, and more preferably from about 25 cm$^3$/g to about 55 cm$^3$/g.

Figure 4:
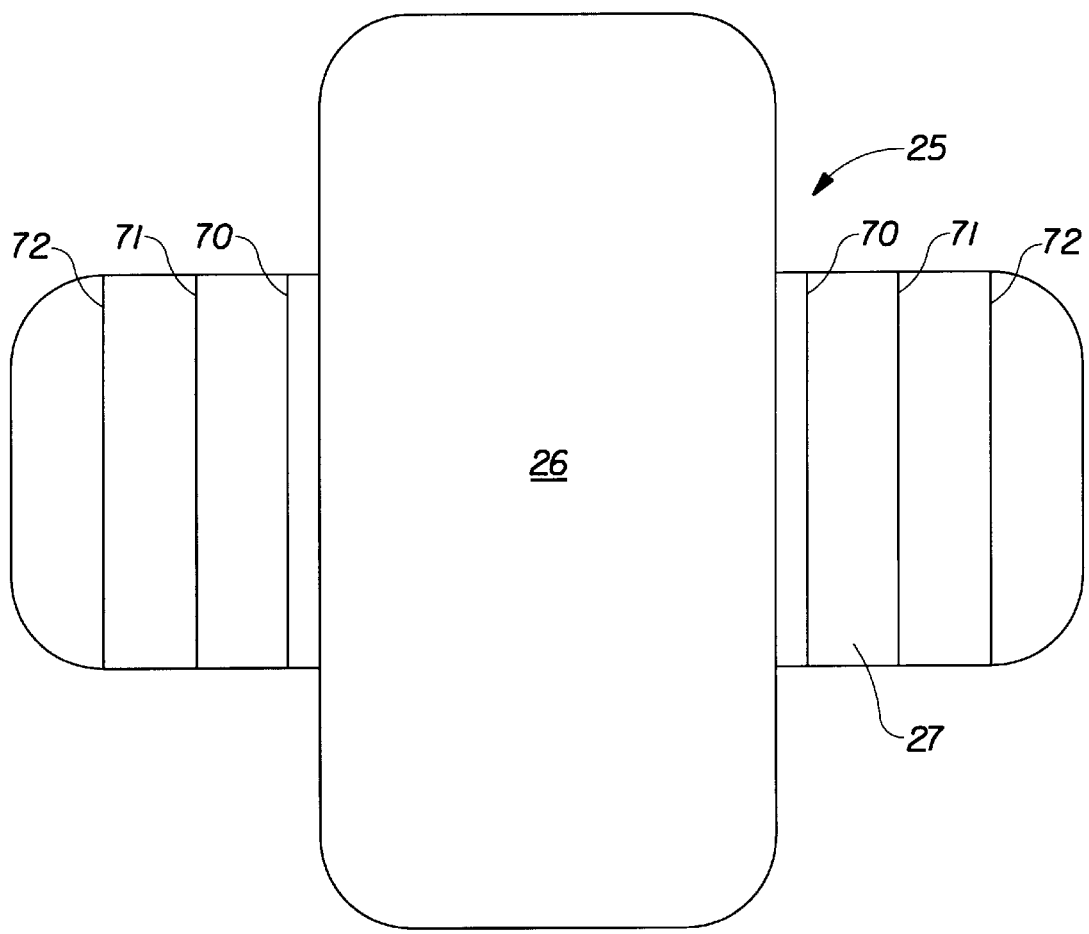
FIG. 4 is a plan view of the absorbent core shown in its pre-folded condition.

The absorbent structure 25 for the incontinence pad 20 is shown in greater detail in FIG. 4 in its flat out pre-folded configuration. The absorbent core 25 of the preferred embodiment comprises two components or layers 26 and 27. The individual layers 26 and 27 may be comprised of the same absorbent material or may be tailored and comprised of different absorbent materials. In addition, the absorbent core 25 may comprise a single component or layer.

In a preferred embodiment the lower absorbent layer 27 comprises a resilient absorbent material. A suitable resilient absorbent material is a high capacity Thermally Bonded Air Laid (TBAL), nonwoven material fabricated from a blend of cellulose fibers, bicomponent fibers, and absorbent gelling material particles. The TBAL material obtained from Walkisoft of Aarhus, Denmark, preferably comprises a homogeneous blend of about 30% flint river fluff (cellulose), 60% Nalco 1180 absorbent gelling material particles obtained from Nalcoa of Naperville, Ill., and 10% Danaklon ES-C 3.3 DTEX X 6 MM bicomponent fibers obtained from Danakion of Varde, Denmark. The TBAL material is formed into a web having a basis weight of about 350 g/m$^2$, and a caliper of about 2.7 mm measured under a load of about 0.1 psi. Other suitable resilient absorbent materials for the lower absorbent layer 27 include but are not limited to absorbent foams, and absorbent sponges.

As shown in FIG. 4, the absorbent components 26 and 27 are shown to form a cross-like shape prior to folding. Alternatively, a single absorbent component or layer may be formed into a cross-like shape similar to that shown in FIG. 4. In FIG. 4, the absorbent layer 26 is shown to be positioned on top of the absorbent layer 27. However, these may be reversed wherein the absorbent layer 27 is placed on top of the absorbent layer 26. The underlying absorbent layer 27 is preferably folded along a series of generally parallel longitudinally extending fold lines 70, 71 and 72, to form a pair of resilient absorbent members 40 disposed in the longitudinal side portions 104. The resilient absorbent members 40 disposed in the longitudinal side portions 104 are arranged in a longitudinally spaced relation to each other between the acquisition component 30 and the topsheet 22. As shown in FIG. 2, the absorbent layer 27 is folded along the generally parallel longitudinally extending fold lines 70, 71, and 72 such that it encapsulates the acquisition component 30 within the longitudinal side portions 104 to form resilient absorbent members 40 which are disposed alongside and on top of the acquisition component 30.

Preferably, the resilient absorbent members 40 are contained solely within the longitudinal side portions 104. This allows the bulk of the absorbent material to be concentrated in the side portions 104 of the incontinence pad 20. As mentioned above, this becomes important as the point of insult typically occurs in the central region 102 and spreads radially therefrom. Since the incontinence pad 20 is typically narrower in width or has a width dimension smaller than its length dimension bodily fluid deposited upon the incontinence pad 20 typically reaches the side or longitudinal edges 110 prior to reaching the end edges 108. Therefore, it is important to have additional capacity in the side portions 104 since there is no where else for the fluid to transmit.

In contrast to other prior art absorbent structures, the blended structure of the resilient absorbent members of the present invention resists collapse when wetted via the inclusion of the bicomponent fibers and the absorbent gelling material particles. Thus, the resilient absorbent members 40 retain their shape when wetted thus forming a seal between the user and the absorbent pad to thereby prevent side leakage or leakage of urine along the longitudinal side edges 110 of the incontinence pad 20.

Since most of the liquid insult is concentrated in the central region 102 it is important that the central region 102 provide at least about 50% of the total absorptive capacity of the incontinence pad 20. In addition, it is important that the longitudinal side portions 104 provide at least about 60% of the central regions 102 absorptive capacity. This configuration allows the incontinence pad 20 to have sufficient capacity within the side portions 104 permitting the acquisition component 30 to fully drain into the resilient absorbent members 40 located within the longitudinal side portions 104. Other executions are suitable wherein the central region 102 provides at least about 60%, more preferably at least about 70%, and most preferably about 80% of the total absorptive capacity of the incontinence pad 20. In addition, in preferred embodiments the longitudinal side portions 104 provide at least about 70% of the central region's absorptive capacity, more preferably about 80%, and most prefer ably at least about 90% of the central region's total absorptive capacity.

The resilient absorbent members 40 provide an improved incontinence pad design having raised side portions which are pressed up against the skin area around the perineal area by the wearer's undergarment thereby forming a gasketing effect leading to close body contact between the wearer and the incontinence pad 20. Liquid is thereby directed toward the middle of the incontinence pad 20 into the acquisition component 30. Prefer ably, the resilient absorbent members 40 have a height as measured from acquisition component of at least about 1 mm, preferably, the resilient absorbent members 40 have a height of from about 2 mm to about 3 mm. However, if the resilient absorbent members 40 are too high they may be uncomfortable for the wearer.

In addition to the gasketing effect mentioned above, the resilient absorbent members 40 also provide an improved gasketing effect after the incontinence pad 20 has been subjected to liquid insult. Upon wetting the absorbent gelling material particles within the resilient absorbent members 40 swell thereby causing the resilient absorbent members 40 to expand. This expansion of the resilient absorbent members 40 presses them into closer contact with the wearer's skin thereby improving the gasketing effect of the incontinence pad 20.

In addition, because the properties of the resilient absorbent members 40 in retaining their shape and acquisition characteristics even when wet, the incontinence pad 20 is capable of acquiring a subsequent gush of liquid without increased likelihood of leakage. Because of its physical properties, the resilient absorbent members 40 also enhance the comfort perceived by the wearer. The resilient absorbent members 40 mainly serve as a storage reservoir in the side regions of the absorbent pad for containing bodily liquids.

The resilient absorbent members 40 of the present invention may be formed in number of ways. As is shown in FIG. 2, the material forming the resilient absorbent members 40 may be folded one layer on top of another to provide the resilient absorbent member 40 with sufficient height. Alternatively, the resilient absorbent members may be formed by rolling the absorbent material into a tubular configuration.

In a preferred embodiment the absorbent layer 26 also comprises a high capacity TBAL nonwoven material fabricated from a blend of cellulose fibers, bicomponent fibers, and absorbent gelling material particles. The TBAL material obtained from Walkisoft of Aarhus, Denmark, preferably comprises a homogeneous blend of about 30% flint river fluff (cellulose), 60% Nalco 1180 absorbent gelling material particles obtained from Nalcoa of Naperville, Ill., and 10% Danaklon ES-C 3.3 DTEX X 6 MM bicomponent fibers obtained from Danakion of Varde, Denmark. The TBAL material is formed into a web having a basis weight of about 350 g/m$^2$, and a caliper of about 2.7 mm measured under a load of about 0.1 psi.

Since the function of the upper absorbent layer 26, (i.e., to absorb bodily fluids), is different from the lower absorbent layer 27, (i.e., to absorb bodily fluids while providing a resilient structure which can be folded to form the resilient absorbent members 40), the absorbent layer 26 need not be comprised of a resilient material. The absorbent layer 26 may be any absorbent means which is capable of absorbing or retaining liquids (e.g., urine). The absorbent layer 26 may be manufactured from a wide variety of liquid-absorbent materials commonly used in incontinence pads and other absorbent articles such as comminuted wood pulp which is generally referred to as airfelt. Examples of other suitable absorbent materials include creped cellulose wadding; melt-blown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. The configuration and construction of the absorbent layer may also be varied (e.g., the absorbent core may have varying caliper zones (e.g., profiled so as to be thicker in the center) hydrophilic gradients, superabsorbent gradients, or lower density and lower average basis weight acquisition zones; or may comprise one or more layers or structures). The total absorbent capacity of the absorbent layer should, however, be compatible with the desired loading and the intended use.

Exemplary absorbent structures for use as the absorbent layer 26 are described in U.S. Pat. No. 4,950,264 issued to Osborn on Aug. 21, 1990; U.S. Pat. No. 4,610,678 issued to Weisman et al. on Sep. 9, 1986; U.S. Pat. No. 4,834,735 issued to Alemany et al. on May 30, 1989; European Patent Application No. 0 198 683, The Procter & Gamble Company, published Oct. 22, 1986 in the name of Duenk, et al.; International Publication No. WO 94/28838, published Dec. 22, 1994 in the name of Palumbo, et al.; and International Publication No. WO 94/01069, published Jan. 20, 1994 in the name of Palumbo, et al. Each of these patents are incorporated herein by reference.

To allow liquids to rapidly flow into the acquisition component 30 of the incontinence pad 20, the resilient members 40 must be in a spaced relation to each other. As shown in FIGS. 1 and 2, the resilient absorbent members 40 are in a longitudinal spaced relation to each other and are located each respectively within the longitudinal side portions 104. (A longitudinal spaced relation is defined as placing the elements lengthwise along the side of the pad so that there is a transverse width dimension separating the elements.) While the resilient absorbent members 40 may be arranged in a number of different ways, a longitudinal spacing arrangement is preferred.

In order to provide an incontinence pad 20 capable of being both comfortable and protective, the resilient absorbent members 40 should be compressible, conformable, and resilient. That is to say, the resilient absorbent members 40 must possess such physical properties so that the forces applied by the action of the wearer will readily cause them to bend, to compress and to conform to a space available for them as the incontinence pad 20 is held adjacent the wearer's body. The resilient absorbent members 40 must be resilient so that each must, without the application of external forces, return to essentially its original size and shape of after the forming forces are removed. Preferably, the material used in the manufacturing the resilient absorbent members 40 possess such a resilience that it will recover at least about 80% of its original volume after it is compressed to about 20% of its original volume when the compressing forces are removed. Most preferably, the material will recover at least about 90% of its original volume after it is compressed about 50% of its original volume when the compressing forces are removed.

Because the incontinence pad 20 is designed to retain its shape during use, the resilient absorbent members 40 must also be essentially unaffected by the presence of liquids such as urine. The resilient absorbent members 40 must retain sufficient inherent resiliency, even when wet, to impart to the elements sufficient elasticity to resist close packing of the fibers thereof and the retention of the characteristics of the three-dimensional structure during use so that the incontinence pad 20 will retain its shape during subsequent gushes.

Because the absorbent gelling material-containing resilient absorbent members 40, require sufficient void volume to rapidly contain large quantities of liquids, it is desirable that the acquisition component be able to contain acceptable quantities of liquid. The acquisition component 30 should, therefore, be manufactured of a material of relatively low density such that it has sufficient void volume in the interstices or capillaries between fibers to contain practical quantities of urine.

In the embodiment shown in FIG. 4, the absorbent core comprises two separate absorptive members 26 and 27. Alternatively, a single material may be used to form the absorbent core. In addition, multiple layers of material, for example, three, four, five or more layer may be used to form the absorbent core.

In the embodiment shown in FIG. 2, the absorbent layer 27 is shown to be folded to provide the resilient absorbent members 40 with two layers of material within the longitudinal side portions 104. Alternatively, the folding sequence can be altered such that the absorbent material 27 provides a single layer in the longitudinal side portions 104 or multiple layers such as three, four, five or more layers in the longitudinal side portions 104. However, while the capacity in the longitudinal side portions 104 may be increased by folding the absorbent material 27 multiple times, the comfort of the incontinence pad 20 may be compromised by the bulk of the pad within the longitudinal side portions 104.

A rewet barrier 50 positioned between the topsheet 22 and the resilient absorbent members 40 is liquid pervious, permitting liquids to readily penetrate through its thickness. The rewet barrier may be joined to the resilient absorbent members 40 by any conventional means for joining webs together such as adhesives, heat bonds, pressure bonds, ultrasonic bonds, dynamic mechanical bonds, or any other suitable attachment means or combinations of these attachment means as are known in the art.

A preferred rewet barrier comprises an apertured, macroscopically expanded three-dimensional, polymeric web. Apertured macroscopically expanded, three-dimensional, polymeric webs are preferred for the rewet barrier 50 because they are pervious to bodily fluids and yet non-absorbent and have a reduced tendency to allow liquids to pass back through and rewet the wearer's skin. Thus, the outer cover of the incontinence pad which is in contact with the body remains dry, thereby reducing body soiling and creating a more comfortable feel for the wearer. Suitable apertured, macroscopically expanded, three-dimensional, polymeric webs are described in U.S. Pat. No. 3,929,135 issued to Thompson on Dec. 30, 1975; U.S. Pat. No. 4,324,246 issued to Mullane et al. on Apr. 13, 1982; U.S. Pat. No. 4,342,314 issued to Radel et al. on Aug. 3, 1982; U.S. Pat. No. 4,463,045 issued to Ahr et al. on Jul. 31, 1984; and U.S. Pat. No. 5,006,394 issued to Baird on Apr. 9, 1991. Each of these patents are incorporated herein by reference.

The incontinence pad 20 is preferably provided with adhesive attachment means 60 as is illustrated in FIG. 2. The adhesive attachment means 60 is illustrated as a wide strip of adhesive positioned on the backsheet 24 and running almost the entire length of the incontinence pad 20. This arrangement is selected for convenience; those skilled in the art can readily select a different pattern for the adhesive attachment means 60. The purpose of the adhesive attachment means 60 is to secure the incontinence pad 20 in the crotch region of the wearer's undergarment. Any adhesive or glue used with sanitary napkins for such a purpose can be used with this invention. Pressure sensitive adhesives are preferred. Suitable adhesives include Century A-305-IV manufactured by Century Adhesive Corporation of Columbus, Ohio and Instant Lok 34-2823 manufactured by National Starch and Chemical Company of Bridgewater, N.J. Suitable adhesive fasteners are also described in U.S. Pat. No. 4,917,697.

Before the incontinence pad is placed in use, the pressure sensitive adhesive is typically covered with a removable release liner 62 in order to keep the adhesive 60 from drying out or adhering to a surface other than the crotch portion of the panty prior to use. Suitable release liner 62 are also described in the above-referenced U.S. Pat. No. 4,917,697. Any commercially available release liners commonly used for such purposes can be utilized herein. Non-limiting examples of suitable release liners 34 are BL30 MG-A SILOX E1-0 and BL30 MG-A SILOX 4P/O both of which are manufactured by the Akrosil Corporation of Menasha, Wis. The incontinence pad of the present invention is used by removing the release liner 62 and thereafter placing the incontinence pad 20 in a panty so that the adhesive 60 contacts the panty. The adhesive 60 maintains the incontinence pad 20 in its position within the panty during use.

The end regions 100 of the incontinence pad 20 preferably have a caliper less than that of the central region 102. Preferably, the end regions 100 have a caliper of less than about 8 mm, more preferably less than about 6 mm, most preferably less than about 4 mm. The caliper within the end regions 100 is important such that the incontinence pad 20 is not too thick that it becomes irritating and therefore uncomfortable for the wearer.

Figure 6:
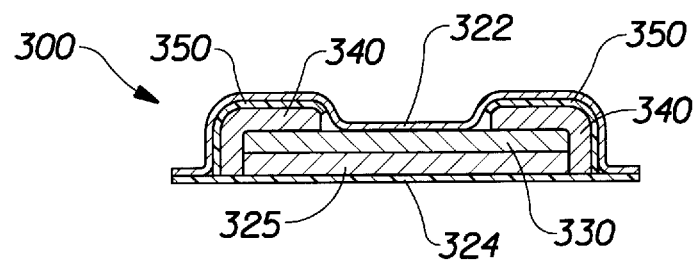
FIG. 6 is a cross-sectional view of another embodiment of an incontinence pad of the present invention.

Referring now to FIG. 6, there is shown another embodiment of an incontinence pad 300 of the present invention. The incontinence pad 300 comprises a liquid pervious topsheet 322, a liquid impervious backsheet 324 joined with the topsheet 322, an absorbent core 325 position between the topsheet 322 and the backsheet 324, an acquisition component 330 positioned between the topsheet 322 and the absorbent core 325, a pair of resilient absorbent members 340 disposed one on each side of the incontinence pad 300, and a rewet barrier 350 positioned between the resilient absorbent members 340 and the topsheet 322. The resilient absorbent members 340 are separate and distinct members from the absorbent core 325.

In other preferred alternative embodiments, the incontinence pad 20 can be provided with an absorbent core that is capable of separating from (or decoupling" from) at least a portion of the acquisition component to provide improved fit and performance. The separation or decoupling of theses components refers to a movement of one component apart from another component in a direction generally perpendicular to the longitudinal and transverse axes, (i.e., in the "Z-direction"). The concept of separation of components of an absorbent article is described in greater detail in U.S. Pat. No. 5,077,906 entitled "Decoupled Sanitary Napkin", issued to Osborn, et al. on Apr. 16, 1992; in PCT International Patent Application Publication No. WO 92/07535 entitled "Sanitary Napkin Having Components Capable of Separation in Use" published in the name of Visscher, et al. on May 14, 1992; and in U.S. patent application Ser. No. 07/874,872 entitled "Generally Thin, Flexible Sanitary Napkin With Stiffened Center" filed Apr. 28, 1992 in the name of Osborn.

The separation of the absorbent core 25 from the acquisition component 30 may alternatively be thought of as a separation of the topsheet 22 from the absorbent core 25. This is because if the absorbent core 25 separates from the acquisition component 30, the topsheet 22, (being disposed on the other side of the acquisition component 30) will also separate from the absorbent core 25.

Figure 7:
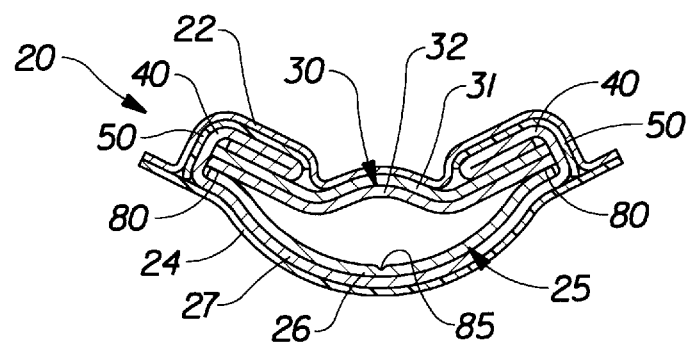
FIG. 7 is a sectional view of the incontinence pad of FIG. 1 showing the separation of the absorbent core from the acquisition component.

The separation or decoupling of the absorbent core 25 from the acquisition component 30 is shown in FIG. 7. The drawings are merely intended to be approximate representations of the configuration that the incontinence pad 20 may take when it is worn. Thus, the separation of these components may occur in manners in addition to those shown in the drawings. The scope of the present invention includes all of these other configurations and manners of separation. In addition, it should also be understood that the size of various components of the incontinence pad 20 may be slightly exaggerated in the drawings. This has been done to more clearly show the separation of the components of the incontinence pad 20.

The separation of the absorbent core 25 from the acquisition component 30 is possible because of the way the absorbent core 25 is joined to the acquisition component 30. The upper layer 26 of the absorbent core 25 is joined to the lowermost acquisition component 32 at junctures 80. The acquisition component 30 is otherwise unattached to the absorbent core 25. The unattached portion of the acquisition component 30 may move apart, separate, or decouple from the absorbent core 25.

To further aid in the separation of the absorbent core 25 from the acquisition component 30, the uppermost layer 26 of the absorbent core 25, which may comprise a relatively stiff material, is preferably provided with an embossed channel, fold or crease. For example, the absorbent layer 26 shown in FIG. 7 is provided with an embossed channel 85 which extends along the longitudinal centerline L. When the incontinence pad 20 is subjected to the lateral compressive forces caused by the thighs of the wearer, the portions of the body facing surface of the absorbent layer 26 on either side of the embossed channel 85 are brought closer together. The unattached portion of the acquisition component 30 separates and lifts from the absorbent core such that the incontinence pad 20, and in particular the topsheet 22 and the acquisition component 30, will conform with the wearer's anatomy. Thus, the incontinence pad 20 is in a position to more readily intercept bodily fluids discharged from the wearer.

Alternatively, the absorbent layer 26 may be provided with a low density or lower basis weight channel which extends along the longitudinal centerline L. Since the portions of the absorbent layer 26 on either side of the low density channel will typically be stiffer than the channel, the absorbent layer 26 will tend to bend along the channel when the incontinence pad 20 is subjected to the lateral compressive forces caused by the thighs of the wearer during use.

Additionally, the absorbent layer 26 may be provided with multiple embossed channels, folds or creases allowing the absorbent layer 26 to bend in numerous configurations. Furthermore, if desired, the absorbent layer 27 may also be provided with one or more channels, folds, or creases to assist the absorbent layer 27 in bending in the desired configuration.

While particular embodiments of the present invention have been illustrated and described, those skilled in the art will recognize that various changes and modifications can be made without departing from the spirit and scope of the invention. It is intended to cover, in the claims, all such modifications that are within the scope of this invention.

What is claimed is:

1. An absorbent article having a pair of end regions, a central region disposed between said end regions having a longitudinal length between about one-fourth to about two-thirds the total longitudinal length of the absorbent article, said central region comprising a pair of spaced apart longitudinal side portions, each longitudinal side portion having a transverse width between about one-eighth to about one-third of the total transverse width of said central region, and a central portion disposed between said longitudinal side portions, said central portion having a transverse width between about one-third to about three-fourths of the total transverse width of said central region, said absorbent article comprising:

a liquid pervious topsheet;

a liquid impervious backsheet joined with said topsheet;

an absorbent core positioned between said topsheet and said backsheet;

an acquisition component positioned between said topsheet and said absorbent core, said acquisition component having a total void volume capacity, said central region providing at least about 50% of said total void volume capacity;

a pair of resilient absorbent members disposed in said longitudinal side portions, said resilient absorbent members arranged in a transversely spaced relation to each other between said acquisition component and said top sheet;

said absorbent article having a total absorptive capacity, said central region providing at least about 50% of said total absorptive capacity, said longitudinal side portions providing at least about 70% of the central region's absorptive capacity.

2. The absorbent article of claim 1 further comprising a rewet barrier positioned between said resilient absorbent members and said topsheet, said rewet barrier comprising an apertured, macroscopically expanded three-dimensional, polymeric web.

3. The absorbent article of claim 1 wherein each of said resilient absorbent members is formed from a resilient material that will recover at least about 80% of its original volume after it is compressed about 20% of its original volume.

4. The absorbent article of claim 1 wherein each of said resilient absorbent members comprises bicomponent fibers.

5. The absorbent article of claim 4 wherein each of said resilient absorbent members comprise cellulose fibers and absorbent gelling material particles.

6. The absorbent article of claim 1 wherein said absorbent core comprises a low basis weight channel.

7. The absorbent article of claim 1 wherein said absorbent core an embossed channel.

8. The absorbent article of claim 1 wherein each of said resilient absorbent members has a height of at least about 1 mm.

9. The absorbent article of claim 1 wherein each of said resilient absorbent members has a height of from about 1 mm to about 2 mm.

10. The absorbent article of claim 1 wherein the longitudinal length of the central region is about one-third of the total longitudinal length of the absorbent article.

11. The absorbent article of claim 1 wherein the transverse width of the central portion is about one-half of the total longitudinal length of the absorbent article.

12. An absorbent article having a pair of end regions, a central region disposed between said end regions having a longitudinal length between about one-fourth to about two-thirds the total longitudinal length of the absorbent article, said central region comprising a pair of spaced apart longitudinal side portions, each longitudinal side portion having a transverse width between about one-eighth to about one-third of the total transverse width of said central region, and a central portion disposed between said longitudinal side portions, said central portion having a transverse width between about one-third to about three-fourths of the total transverse width of said central region, said absorbent article comprising:

a liquid pervious topsheet;

a liquid impervious backsheet joined with said topsheet;

an acquisition component positioned between said topsheet and said backsheet, said acquisition component having a total void volume capacity, said central region providing at least about 50% of said total void volume capacity;

an absorbent core positioned between said acquisition component and said backsheet, a portion of said absorbent core being folded upon said acquisition component along a first pair of generally parallel longitudinally extending fold lines to form a pair of resilient absorbent members which encapsulate said acquisition component within said longitudinal side portions, said resilient absorbent members arranged in a transversely spaced relation to each other between said acquisition component and said topsheet;

said absorbent article having a total absorptive capacity, said central region providing at least about 50% of said total absorptive capacity, said longitudinal side portions providing at least about 70% of the central region's absorptive capacity.

13. The absorbent article of claim 12 further comprising a rewet barrier positioned between said resilient absorbent members and said topsheet, said rewet barrier comprising an apertured, macroscopically expanded, three-dimensional polymeric web.

14. The absorbent article of claim 12 wherein each of said resilient absorbent members is formed from a resilient material that will recover at least about 80% of its original volume after it is compressed about 20% of its original volume.

15. The absorbent article of claim 12 wherein each of said resilient absorbent members comprises bicomponent fibers.

16. The absorbent article of claim 12 wherein each of said resilient absorbent members has a height of at least about 1 mm.

17. The absorbent article of claim 12 wherein each of said resilient absorbent members has a height of from about 1 mm to about 2 mm.

18. The absorbent article of claim 12 wherein the longitudinal length of the central region is about one-third of the total longitudinal length of the absorbent article.

19. The absorbent article of claim 12 wherein the transverse width of the central portion is about one-half of the total transverse width of the absorbent article.

* * * * *